US007015044B2

(12) United States Patent
Han et al.

(10) Patent No.: US 7,015,044 B2
(45) Date of Patent: Mar. 21, 2006

(54) DIAGNOSTIC FOR EARLY STAGE ALZHEIMER'S DISEASE

(75) Inventors: Xianlin Han, Clayton, MO (US); David M. Holtzman, St. Louis, MO (US)

(73) Assignee: Washington University, St. Louis, MO (US)

( * ) Notice: Subject to any disclaimer, the term of this patent is extended or adjusted under 35 U.S.C. 154(b) by 484 days.

(21) Appl. No.: 10/317,031

(22) Filed: Dec. 10, 2002

(65) Prior Publication Data
US 2003/0180959 A1 Sep. 25, 2003

Related U.S. Application Data

(60) Provisional application No. 60/339,188, filed on Dec. 10, 2001.

(51) Int. Cl.
*G01N 33/92* (2006.01)
*G01N 24/00* (2006.01)
(52) U.S. Cl. .......................... 436/71; 436/173; 436/811
(58) Field of Classification Search ................ 436/71, 436/173, 811
See application file for complete search history.

(56) References Cited

U.S. PATENT DOCUMENTS

2001/0044126 A1  11/2001  Holtzman et al. ......... 435/7.92

FOREIGN PATENT DOCUMENTS

WO    WO 01/49875    7/2001

OTHER PUBLICATIONS

Bosio, A., et al., "Functional Breakdown of the Lipid Bilayer of the Myelin Membrane in Central and Perioheral Nervous System by Disrupted Galactocerebroside Synthesis" Proc. Natl. Acad. Sci. USA (1996) 93:13280-13285.

Coetzee, T., et al., "Myelination in the Absence of Galactocerebroside and Sulfatide: Normal Structure with Abnormal Function and Regional Instability" Cell (1996) 86:209-219.

Fredman, P., et al., "Sulfatide as a Biochemical Marker in Cerebrospinal Fluid of Patients with Vascular Dementia" Acta Neurol. Scand. (1992) 85:103-106.

Galasko, D., et al., "High Cerebrospinal Fluid Tau and Low Amyloid β42 Levels in the Clinical Diagnosis of Alzheimer Disease and Relation to Apolipoprotein E Genotype" Arc. Neurol. (1998) 55:937-945.

Gottfries, C-G., et al., "Membrane Components Separate Early-Onset Alzheimer's Disease from Senile Dementia of the Alzheimer Type" Int. Psycho-Geriatrics (1996) 8:365-372.

Han, X. et al., "Substantial Sulfatide Deficiency and Ceramide Elevation in Very Early Alzheimer's Disease: Potential Role in Disease Pathogenesis" J. Neurochem. (2002) 82:809-818.

Hannun, Y.A. et al., "Functions of Ceramide in Coordinating Cellular Reponses to Stress" Science (1996) 274:1855-1859.

Hess, B., et al., Proc. "Phenotype of Arylsulfatase A-Deficient Mice: Relationship to Human Metachromatic Leukodystrophy" Natl. Acad. Sci. USA (1996) 93:14821-14826.

Kolesnick, R.N., et al., "Regulation of Ceramide Production and Apoptosis" Ann. Rev. Physiol. (1998) 60:643-665.

(Continued)

*Primary Examiner*—Yelena G. Gakh
(74) *Attorney, Agent, or Firm*—Morrison & Foerster LLP (57) ABSTRACT

A method for diagnosing Alzheimer's disease even at early stages by assessing the levels of sulfatides or its metabolites in biological fluids is disclosed.

15 Claims, 11 Drawing Sheets

OTHER PUBLICATIONS

Morris, J.C., "The Clinical Dementia Rating (CDR): Current Version and Scoring Rules" Neurology (1993) 43:2412-2414.

Paola, M.D., et al., "Ceramide Interaction with the Respiratory Chain of Heart Mitochondria" Biochemistry (2000) 39:6660-6668.

Svennerholm, L., "Krabbe Disease: A Galactosylsphingosine (Psychosine) Lipidosis" J. Lipid Res. (1980) 21:53-64.

International Preliminary Examination Report, mailed on Oct. 29, 2003, for PCT patent application No. PCT/US02/39567, filed on Dec. 10, 2002, 5 pages.

Majocha et al., J. Neurochem. (1989) 53(3):953-961 (abstract).

Sorbi et al., Gerontology (1987) 33:197-202.

Supplementary European Search Report for EP 02 80 4772, mailed on Dec. 10, 2004, 1. page.

Tarvonen-Schröder et al., Dement. Geriatr. Cogn. Disord. (1997) 8:174-179.

Gottfries et al. (1986) *Prog Neuropsychopharmacol Biol Psychiatry* 10(3-5):405-413 (Abstract).

Mass spectra of lipid extracts of CSF from a cognitively-normal person (A) and a very mild AD patient (B). PI represents phosphatidylinositol and ST represents sulfatide.

DIAGNOSTIC FOR EARLY STAGE ALZHEIMER'S DISEASE

RELATED APPLICATION

This application claims priority under 35, U.S.C. §119(e) to U.S. provisional application No. 60/339,188 filed 10 Dec. 2001. The contents of this application are incorporated herein by reference.

ACKNOWLEDGEMENT OF GOVERNMENT SUPPORT

At least a portion of this work was supported by National Institutes of Health (NIH) contract NIH-AG05681. The U.S. government has certain rights in this invention.

TECHNICAL FIELD

The invention relates to methods and materials useful in diagnosing very early stage Alzheimer's disease. More specifically, it concerns assessing sulfatides in the cerebrospinal fluid, or other body fluid, whereby a decreased level of sulfatides or an increase in its metabolites indicates the presence of Alzheimer's disease.

BACKGROUND ART

The diagnosis of Alzheimer's disease, especially in the early stages, is notoriously difficult. Postmortem analysis of the brain shows the presence of neuritic plaques and neurofibulary tangles. Studies of brain tissue in the past have focused on gray matter pathology, but white matter has also been implicated in more recent studies. White matter in Alzheimer's subjects shows a dramatic loss of myelin and axons, DNA fragmentation, and plasmalogen deficiency in early stages of the disease. ("Plasmalogen" refers to a class of phospholipid enriched in myelin.) Most Alzheimer's patients show evidence of white matter degeneration and loss of oligodendrocytes (Morris, J. C., *Neurology* (1993) 43:2412–2414).

Figure 1:
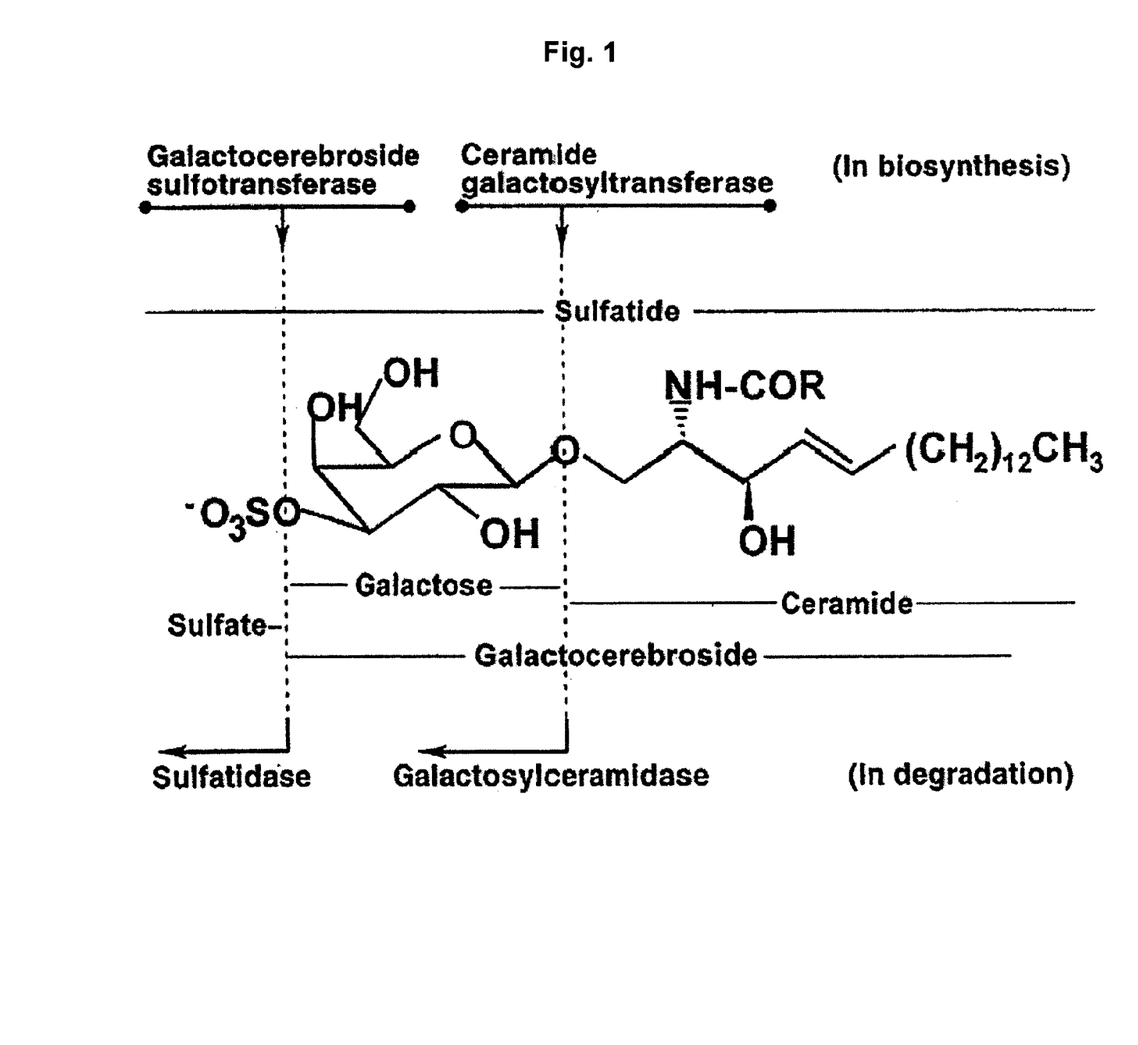
FIG. 1 shows the structure of sulfatides in general and the mechanisms for synthesis and breakdown of this class of compounds.

Sulfatides are a class of sulfated galactocerebrosides. A general structure for sulfatides is shown in FIG. 1. The various sulfatides differ only in the fatty acid represented by RCO in the structure. Sulfatides are synthesized through the mediation of ceramidase galactosyl transferase with subsequent sulfation mediated by galactocerebroside sulfotransferase. They are degraded, ultimately to ceramides, by the action of sulfatidase and galactosyl ceramidase. Sulfatides are important in the regulation of cell growth, protein trafficking, signal transduction, cell adhesion, neuronal plasticity and cell morphogenesis and are synthesized exclusively by oligodendrocytes in the central nervous system. They are present predominantly in the myelin sheath surrounding the axons and are present both in gray matter and white matter in the brain.

It has previously been shown that a deficiency in sulfatidase leads to an accumulation of sulfatides and to metachromatic leukodystrophy (Hess, B., et al., *Proc. Natl. Acad. Sci. USA* (1996) 93:14821–14826). A galactosyl ceramidase deficiency also leads to the accumulation of sulfatides as well as galactocerebrosides in Krabbe's disease (Svennerholm, L., *J. Lipid Res.* (1980) 21:53–64). Further, knockout mice lacking ceramide galactosyl transferase show deficiencies in sulfatides and galactocerebrosides and generally die by three months and demonstrate abnormal axonal function. (Bosio, A., et al., *Proc. Natl. Acad. Sci. USA* (1996) 93:13280–13285; Coetzee, T., et al., *Cell* (1996) 86:209–219.)

It is also known that the ceramides, which are sulfatide degradation products are lipid second messengers and mediate inflammatory cytokines and growth factors so that the accumulation of ceramides results in up-regulation of cytokines, generation of reactive oxygen species, interruption of the mitochondrial respiratory chain and apoptosis (Hannun, Y. A., et al., *Science* (1996) 274:1855–1859; Kolesnick, R. N., et al., *Ann. Rev. Physiol.* (1998) 60:643–665; Paola, M. D., et al, *Biochemistry* (2000) 39:6660–6668).

Gottfries, C-G., et al., *Int. Psycho-Geriatrics* (1996) 8:365–372 describe studies which purport to distinguish the membrane components in brain of subjects with Alzheimer's disease from those with senile dementia of the Alzheimer's type (SDAT). SDAT and Alzheimer's disease are presently classified together since they appear to differ only in the age of onset of dementia; the onset in "pure Alzheimer's disease" is at an earlier age than that of SDAT. Nevertheless, this study showed that phospholipids, cholesterol, cerebroside and sulfatides were reduced in the frontal lobe white matter in the SDAT group as compared to age-matched controls and Alzheimer's patients. Levels of sulfatides in body fluids such as cerebrospinal fluid, blood, or urine in Alzheimer's patients or controls were not measured.

In a more recent publication, Han, X., et al., *J. Neurochem.* (2002) 82:809–818 further examined the status of sulfatide both in gray matter and white matter. This study, by the group of which the present inventors are members, showed that sulfatides were depleted both in gray matter and white matter in Alzheimer's subjects with very mild dementia, mild, and severe dementia, whereas other major classes of lipid, except plasmalogen were not altered. It was also established that there was no deficiency in the biosynthesis of sulfatides in these individuals and that the content of ceramides was elevated in the white matter. The authors concluded that the decrease in sulfatides was associated with Alzheimer's pathology even in very early stages in the gray and white matter of the brain. No measurements were taken of body fluids of any kind.

Fredman, P., et al., *Acta Neurol. Scand.* (1992) 85:103–106 measured sulfatides in the cerebrospinal fluid of patients with vascular dementia (i.e., dementia caused by stroke) and showed that the sulfatide concentrations in the patients with vascular dementia were at a significantly higher level than those in controls and in the Alzheimer's disease group. The levels in Alzheimer's patients and in controls appeared to be similar. The sulfatide levels in the group with vascular dementia were 307±118 nm/l while that in controls was 145±86 nm/l and in Alzheimer's patients 178±79 nm/l. The authors suggest that the elevation in sulfatide concentration reflects demyelination.

Alternative diagnoses for Alzheimer's disease and early stages thereof which measure components of biological fluids have been described in PCT publication WO 01/49875 and U.S. publication No. 2001/0044126A1 incorporated herein by reference. These documents describe assays in cerebrospinal fluid and blood which are predictive of Alzheimer's disease. These assays involve the levels of circulating amyloid-beta (Aβ) peptide in the blood and in the cerebrospinal fluid (CSF). The Aβ peptide in circulating form is composed of 39–43 amino acids (mostly 40 or 42 amino acids) and results from the cleavage of a common precursor, amyloid precursor protein, designated APP. It was found that the ratio of $A\beta_{40}$ to $A\beta_{42}$ is elevated in individuals with Alzheimer's disease or a propensity therefor. The total circulating levels of Aβ peptide, however, do not differ in Alzheimer's patients and in normal individuals. While statistically this method is helpful, there is some overlap in the values of this ratio between normal and Alzheimer's subjects.

It has also been shown that $A\beta_{42}$ decreases and tau protein increases in patients with moderate to severe clinical Alzheimer's disease (Galasko, D., et al., *Arc. Neurol.* (1998) 55:937–945).

A potential dramatic improvement in this assay is described in U.S. Provisional Applications 60/313,221 filed 17 Aug. 2001 and 60/334,987 filed 23 Oct. 2001, and incorporated herein by reference. In this method, antibodies that sequester Aβ peptide from its bound circulating form in blood alter the clearance of soluble and bound forms of Aβ in the central nervous system and alter the levels of circulating Aβ peptides in the blood when the subject is in clinical or preclinical stage of Alzheimer's. Thus, the level of $A\beta_{40}$, $A\beta_{42}$ or the ratio of $A\beta_{40}/A\beta_{42}$ in the blood of the subject can be measured after injecting these antibodies and an elevation in any of these is indicative of Alzheimer's disease. This method, however, has not yet been assessed in human patients.

The present invention offers a method which clearly separates patients in even the very early stages of Alzheimer's disease from normal subjects. Virtually no overlap occurs between values obtained in subjects who are normal as compared to those with early stage Alzheimer's disease.

DISCLOSURE OF THE INVENTION

The invention is directed to a method to diagnose Alzheimer's disease at a very early or later stage using sulfatides in body fluids such as cerebrospinal fluid (CSF), blood, including plasma, or urine as an index. A decrease in the level of sulfatides in these fluids is positively correlated with the presence of Alzheimer's disease.

Thus, in one aspect, the invention is directed to a method to identify a subject with the condition of Alzheimer's disease or a propensity therefor, including early stage Alzheimer's disease, which method comprises measuring the level of sulfatides in the body fluid of said subject, whereby a subject whose level of sulfatides in said fluids is statistically lower than the level in normal subjects is identified as an individual with Alzheimer's disease. In addition, levels of ceramides and other sulfatide metabolites can be measured instead of or in addition to the sulfatides. Generally, an increased level of at least one metabolite is indicative of an individual with Alzheimer's propensity or disease.

If desired, the level of sulfatides as measured can be normalized with regard to other lipid components whose levels are not altered by the disease or conditions, such as the levels of phosphatidyl inositol. Total sulfatides, or a selected individual sulfatide can be measured.

BRIEF DESCRIPTION OF THE DRAWINGS

FIGS. 9A–9E show the results obtained from CDR 0 and CDR 0.5 patients using various parameters measured in the cerebrospinal fluid as well as the results of psychological tests.

MODES OF CARRYING OUT THE INVENTION

The invention employs biological fluids as the biological samples for assessing sulfatide or ceramide levels as measures of the presence of Alzheimer's disease in the subject. Preferably, the biological fluid is CSF, but blood, plasma, or urine could also be used. Desirably, the biological fluid is first extracted to obtain a lipid fraction for evaluation of the level of sulfatides (or ceramides). However, depending on the method employed for assessing the level of sulfatides (and/or ceramides), such extraction may not be necessary. The sample ultimately used for the assessment may be subjected to fractionation procedures to obtain the most convenient ultimate sample for measurement The invention resides in the discovery that the level of sulfatides, including individual sulfatides, is significantly decreased in body fluids including CSF in a reliable manner in subjects who have Alzheimer's disease, even at very early stages. The stage of the disease can be measured by trained health care providers, with a clinical dementia rating (CDR). This measurement (CDR) shows a score of 0 where there is no dementia, 0.5 when the individual has very mild dementia, 1 for mild dementia, 2 for moderate dementia and 3 for severe dementia. (Morris, J. C., *Neurology* (1993) 43:2412–2414.) By correlating these ratings with neuropathological findings, the diagnostic accuracy for Alzheimer's disease appears to be 93% (Morris, J. C., et al., *Neurology* (1996) 46:707–719; Berg, L., et al., *Arch. Neurol.* (1998) 55:326–335). The present invention allows accurate diagnosis of the presence of, or propensity for, Alzheimer's disease even at the very mild dementia stage of CDR 0.5. This stage of abnormality is also called mild cognitive impairment (MCI).

The methods described by the invention are particularly advantageous since, in addition to showing statistically significant differences in mean values between groups of tested individuals, the degree of overlap in the results derived from populations with normal cognition and those with mild cognitive impairment is extremely low. Thus, the measurement of the appropriate sulfatide level in the biological fluids of a single individual can effectively be used to evaluate the state of that individual. In the case of other prior art measurements, the measurement of the value for a particular individual becomes almost meaningless in view of the high degree of overlap among the results from the two populations.

The level of sulfatides or of an individual sulfatide in a subject may be assessed as a total concentration, but is preferably normalized to the levels of a component which does not vary with the presence of the disease. The levels of phospholipids in general, cholesterol, and cerebrosides are similar in Alzheimer's patients and normal individuals, but levels of these lipids may vary among particular individuals or with the conditions of the assay. Thus, a more accurate assessment for the levels of sulfatides may be obtained by normalizing the sulfatide levels measured to one of these indicators. A particularly preferred and convenient substance for such normalization is the level of phosphatidyl inositol. Factors independent of Alzheimer's disease which cause similar variations in levels of phosphatidyl inositol are expected also to cause variations in the levels of sulfatides. Thus, by taking this ratio, this source for possible error is eliminated.

The levels of sulfatides and, if desired, normalizing components may be measured by any convenient method. Such measurements may include immunoassay methods using specific antibodies or fragments for detection of the various components, chromatographic separation techniques and measurements of individual fractions, or any other suitable method. A particularly preferred and convenient method is electrospray ionization mass spectrometry (ESI-MS) using the lipid extracts per se. This method includes identifying individual species by ESI tandem mass spectrometry. This method is described in detail by Han, X., et al., *Proc. Natl. Acad Sci. USA* (1994) 91:10635–10639; Han, X., et al., *Biochemistry* (1996) 35:5822–5832; and Han, X., et al., *J. Neurochem.* (2001) 77:1168–1180. The contents of these documents are incorporated herein by reference.

Thus, to identify an individual as an Alzheimer's subject, a biological fluid sample is obtained from the subject, subjected, if desired, to fractionation procedures, and assessed for the level of sulfatides, or for an individual sulfatide. The sulfatide level may, if desired, be normalized with regard to a different lipid component, known not to vary with Alzheimer's disease presence, preferably phosphatidyl inositol. The level of sulfatides thus obtained is compared with the values associated with normal individuals; comparison with a single normal individual is possible but it is preferred that a statistical value for the normal population be obtained using an appropriately sized sample. If normalized levels are used, one suitable comparison is based on the ratio of sulfatide to the normalizing substance. For example, the CSF of normal individuals shows a ratio of sulfatides/phosphatidyl inositol of approximately 0.88 based on a sample of 19 normal subjects.

Regardless of the method used for comparison, a decrease in the level of sulfatides in the biological fluid of an individual, relative to control subjects of the same age, identifies that individual as someone with Alzheimer's disease, even in very early clinical stages.

Alternatively, using similar techniques, the levels of ceramide and/or other sulfatide metabolites can be used as an index for the presence of Alzheimer's disease.

The following examples are intended to illustrate but not to limit the invention.

EXAMPLE 1

Levels of Sulfatides and Ceramides in Brain Tissue

Brain tissue samples were taken from subjects who, at the time of death, had various CDR scores and were matched for age of death and postmortem interval. Lipids from individual samples were prepared in the presence of 14:1–14:1 phosphatidyl choline (29 nm/mg protein); 14:0–16:0 phosphatidyl glycerol (PG) (10 nm/mg protein), perdeuterated N-18:0 galactocerebrosides (30 nm/mg protein) and N-17:0 ceramides (5 nm/mg protein) which were used as internal standards for quantitating choline-containing phospholipids, sulfatides, galactocerebrosides, and ceramide respectively. This method was described previously by Han, X., et al., *J. Neurochem.* (2001) 77:1168–1180.

The lipid extracts were analyzed by ESI-MS as described hereinabove.

More specifically, sulfatides in the lipid extracts were prepared by the method of Bligh, E. G., et al., *Can. J. Biochem. Physiol.* (1959) 37:911–917. Sulfatides in the lipid extracts were determined by negative ion ESI-MS and identified by tandem mass spectrometry as described by Hsu, F. F., et al., *Biochim. Biophys. Acta.* (1998) 1392: 202–216, incorporated herein by reference. Sulfatides were directly quantitated by comparison of individual peak intensities with an internal standard (i.e., PG) after correction for $^{13}C$ isotope effects and ionization efficiency factor. The efficiency factor was obtained by measuring the slope of a linear correlation ($\gamma^2$=0.994) of the concentration profile between N-16:0 sulfatide and the internal standard. (A correction factor of 1.385 was then applied.)

Figure 2A:
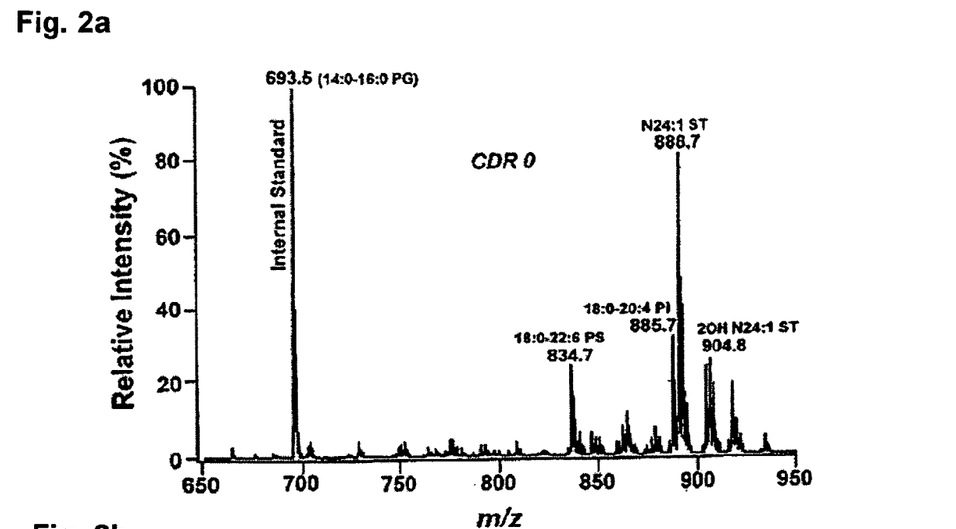
FIGS. 2A and 2B show a comparison of ESI-MS results of lipid extracts from temporal gray matter from a normal subject with results from a subject with very mild Alzheimer's dementia.
Figure 2B:
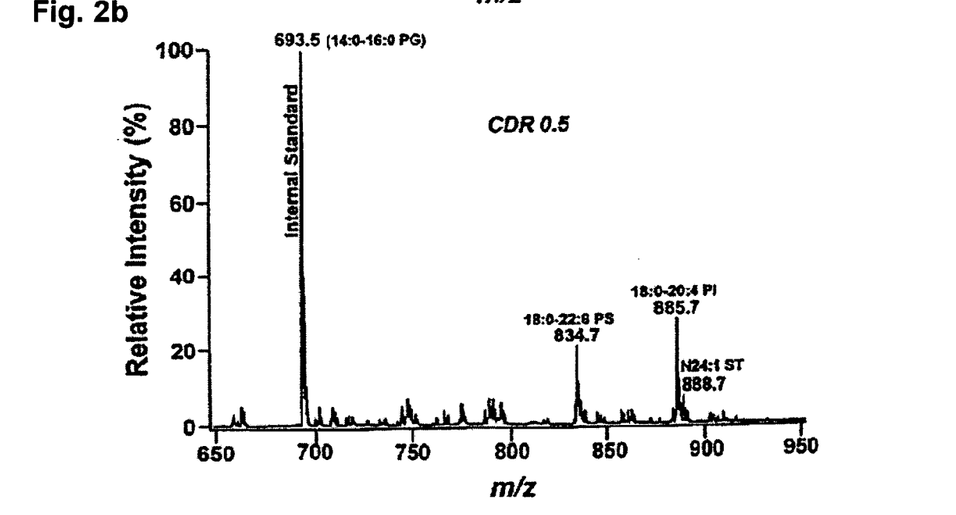

The results of the ESI-MS of the chloroform extract of superior temporal cortex gray matter from a CDR 0 subject as compared to a CDR 5 subject are shown in FIGS. 2A and 2B. FIG. 2A shows the CDR 0 subject has a total sulfatide mass of 42.1±8.8 nm/mg; N-24:1 sulfatide was the major species. The sulfatide content in the cerebral, frontal and parietal gray matter gave essentially identical results, but the sulfatide content in cerebellar gray matter was considerably less representing 17% of that found in cerebral gray matter. The profiles obtained from white matter were substantially similar to those shown in FIG. 2A; however, the total sulfatide in white matter of all cerebral regions was almost three times that in cerebral gray matter.

FIG. 2B shows a comparable ESI-MS for a subject with a CDR of 0.5. It is immediately apparent that the levels of sulfatides are greatly diminished. When a chloroform extract of superior temporal cortex gray matter, similar to that in FIG. 2A was employed, the level of sulfatides dropped to 3.2±0.8 nm/mg protein, a reduction of 92%.

Figure 3A:
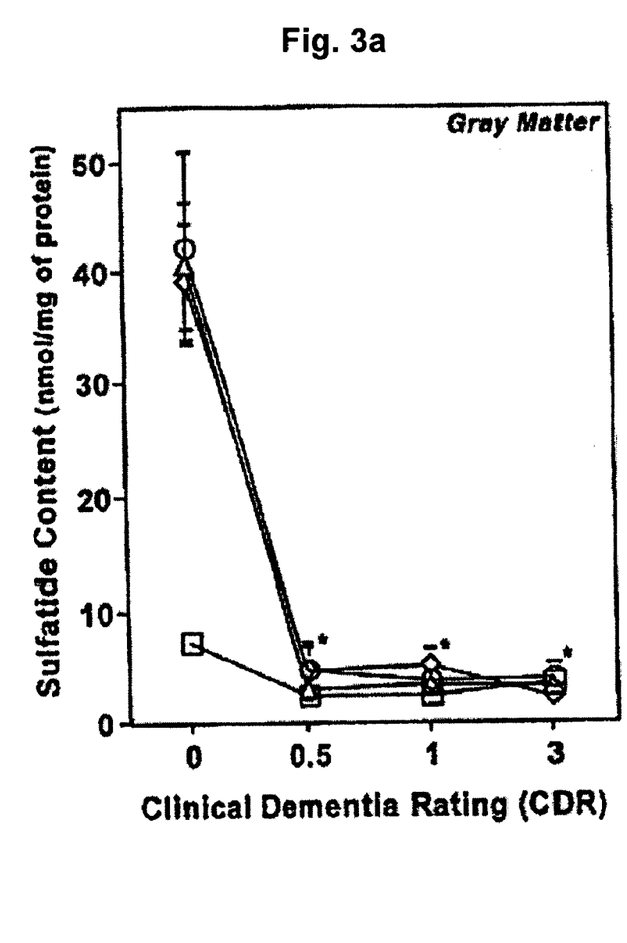
FIGS. 3A and 3B show graphical representations of sulfatide content in cerebral and cerebellar gray and white matter correlated with clinical dementia ratings.
Figure 3B:
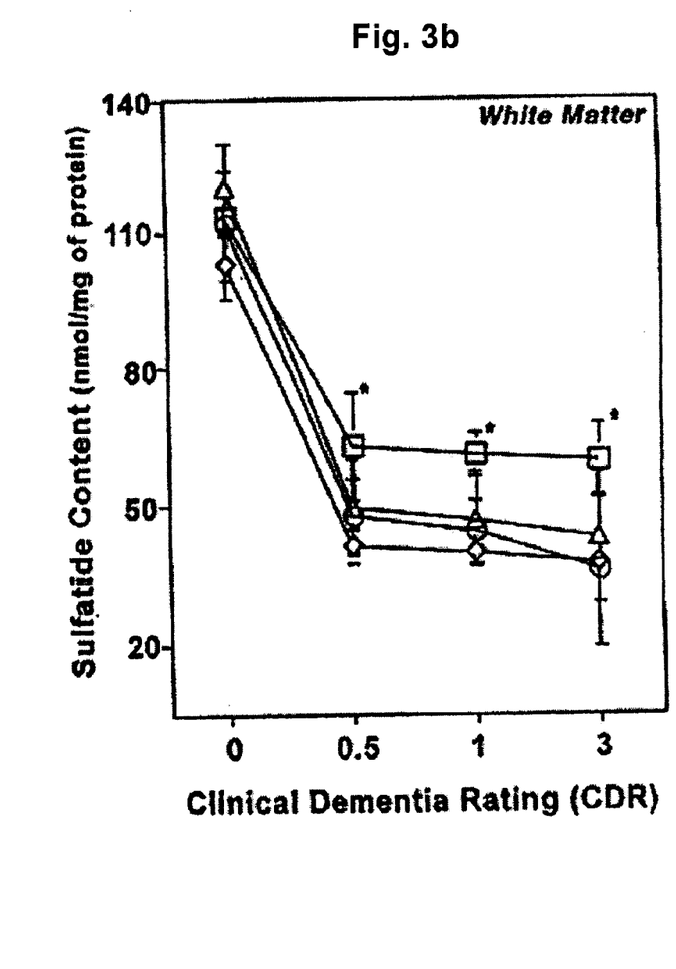

FIGS. 3A and 3B summarize the results obtained for gray matter and white matter as a function of CDR. The total content of sulfatide in chloroform extracts of cerebral frontal (diamonds), temporal (circles), parietal (triangles), and cerebellar (squares) gray matter (FIG. 3A) and white matter (FIG. 3B) was determined using negative ion ESI-MS as described above. The data were normalized to the protein content. It is apparent that a dramatic decrease occurs between normals and very early stage dementia and that the levels are similar at all stages of dementia.

It was also found that there was no alteration in the level of phosphatidylserine (PS) or phosphatidylinositol (PI) between the samples (FIGS. 2A and 2B).

Figure 4A:
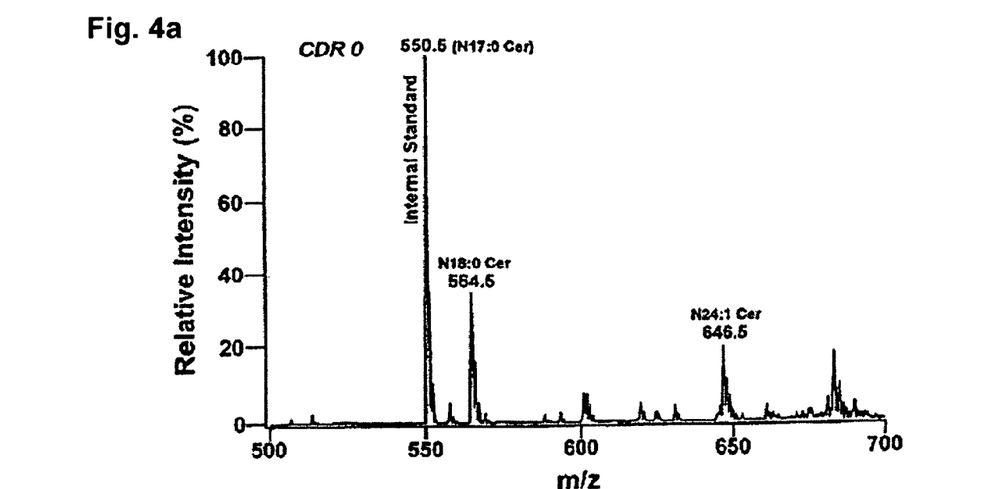
FIGS. 4A and 4B show comparison of negative ion ESI mass spectra of lipid extracts from temporal white matter from a normal and an Alzheimer's disease subject to show ceramide levels.
Figure 4B:
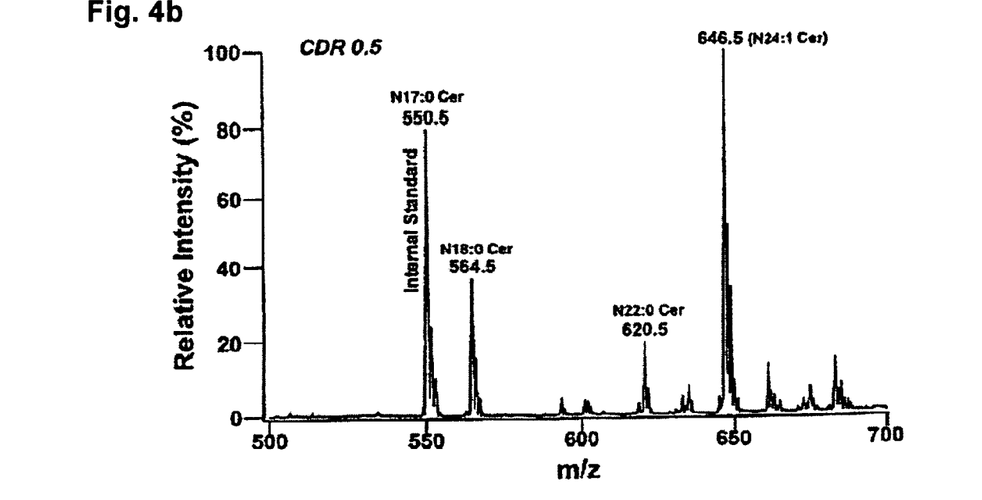

Similar procedures were used to determine ceramide content as shown in FIGS. 4A (CDR 0) and 4B (CDR 0.5). CDR 0 subjects had two major species of ceramide corresponding to N-18:0 and N-24:1 ceramide; the total ceramide mass was 2.59±0.56 nm/mg protein in superior temporal white matter. The ceramide content of white matter from all examined brain regions was essentially identical in the CDR 0 subjects.

However, as shown in FIG. 4B, the total mass of ceramides in the CDR 0.5 subject was 8.7 nm/mg protein, an increase of 3.3-fold; the majority of the increase was of N-24:1 ceramide.

Figure 5A:
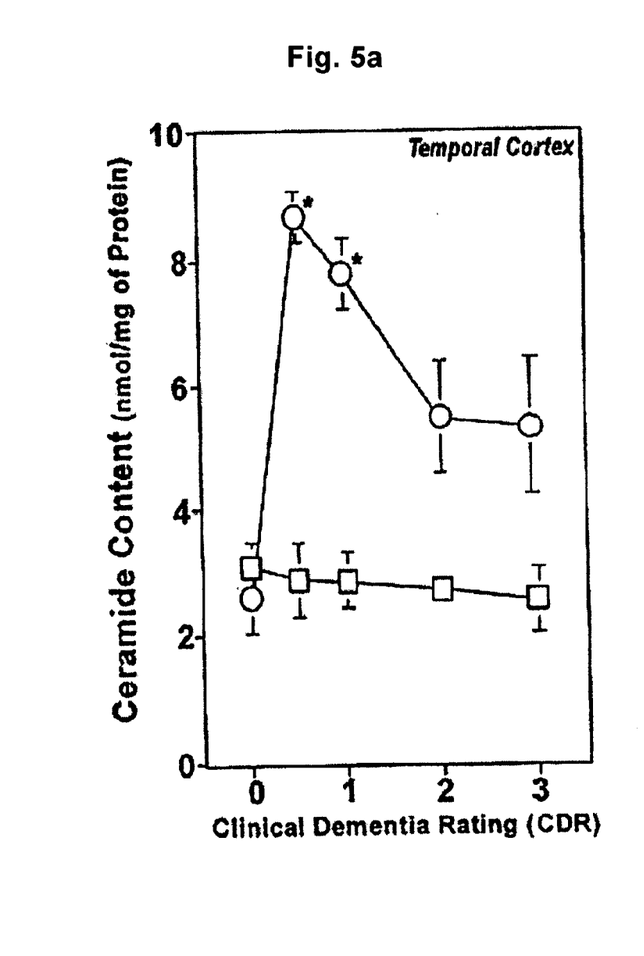
FIGS. 5A and 5B show correlation of ceramide content in gray and white matter with clinical dementia ratings.
Figure 5B:
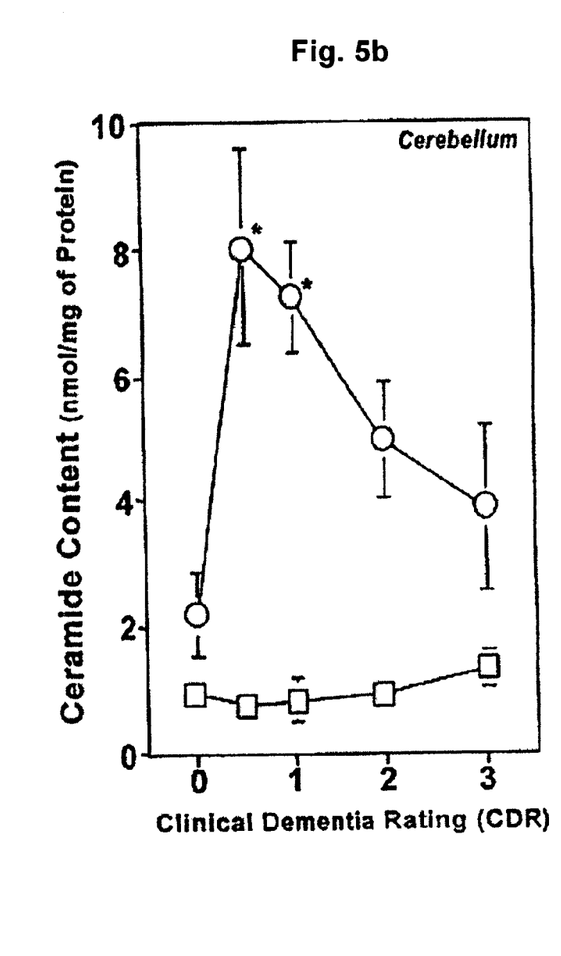

FIGS. 5A and 5B show ceramide content as a function of CDR in the temporal cortex and the cerebellum in both gray matter and white matter. FIG. 5A shows variations in the ceramide content of the temporal cortex white matter (circles) and gray matter (squares); FIG. 5B shows the content of the cerebellar white matter (circles) and gray matter (squares). As shown ceramide content of gray matter appears not to change, with a change in CDR while the white matter content is highly elevated at CDR 0.5 but diminishes as CDR score increases.

Figure 6A:
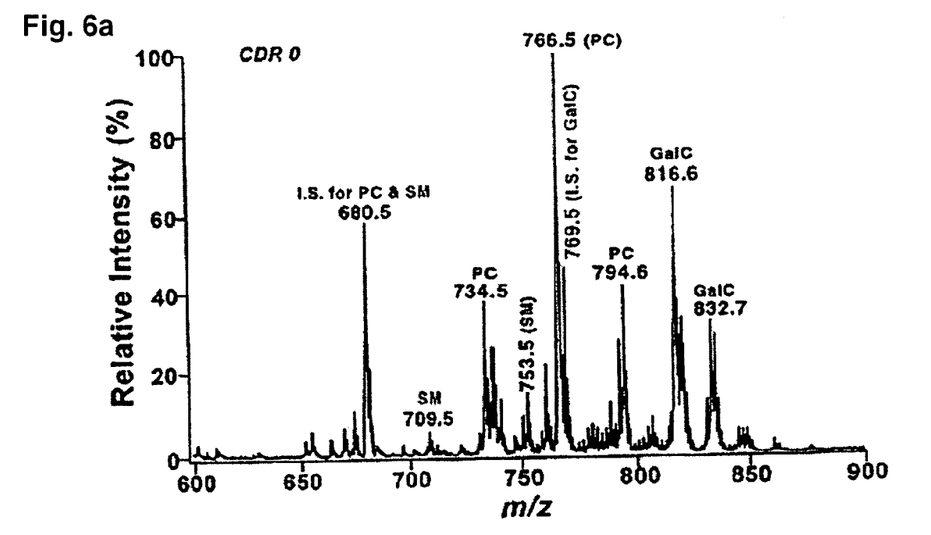
FIGS. 6A and 6B show representative positive ion ESI mass spectra on lipid extracts from temporal white matter of a cognitively normal and a mild Alzheimer's disease subject.
Figure 6B:
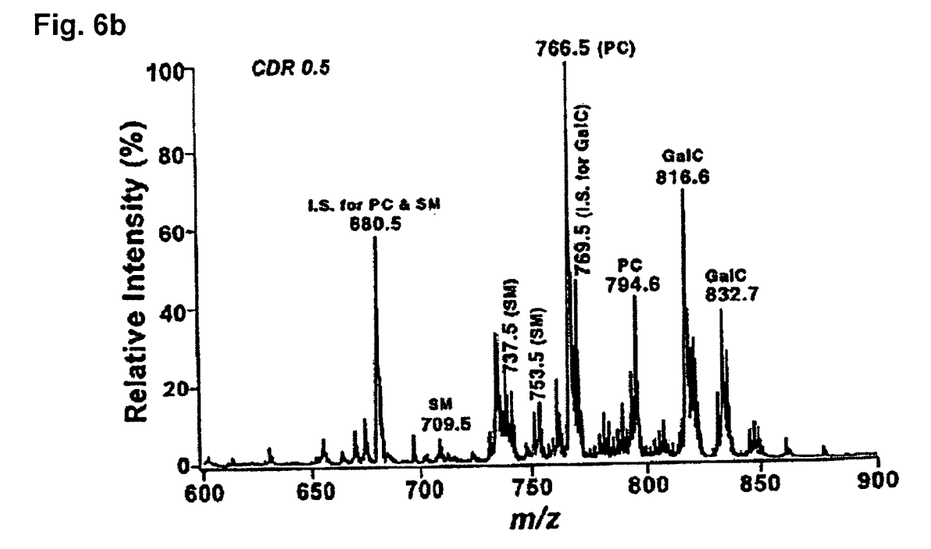

This study also measured sphingomyelin and galactocerebrosides, which are also possible degradation products of sulfatides. Using positive ion ESI-MS, these results are shown in FIGS. 6A (CDR 0) and 6B (CDR 0.5) for lipid extracts of the white matter of the superior temporal cortex. As shown, the values for these compounds as well as for phosphatidylcholine were substantially similar for CDR 0 and CDR 0.5 subjects, the values were approximately 410, 138, 330 nm/mg protein, respectively for CDR 0. Similar comparative results were found with other examined brain tissue samples including gray and white matter of cerebral and cerebellar regions, although there were differences between these regions per se.

Figure 7:
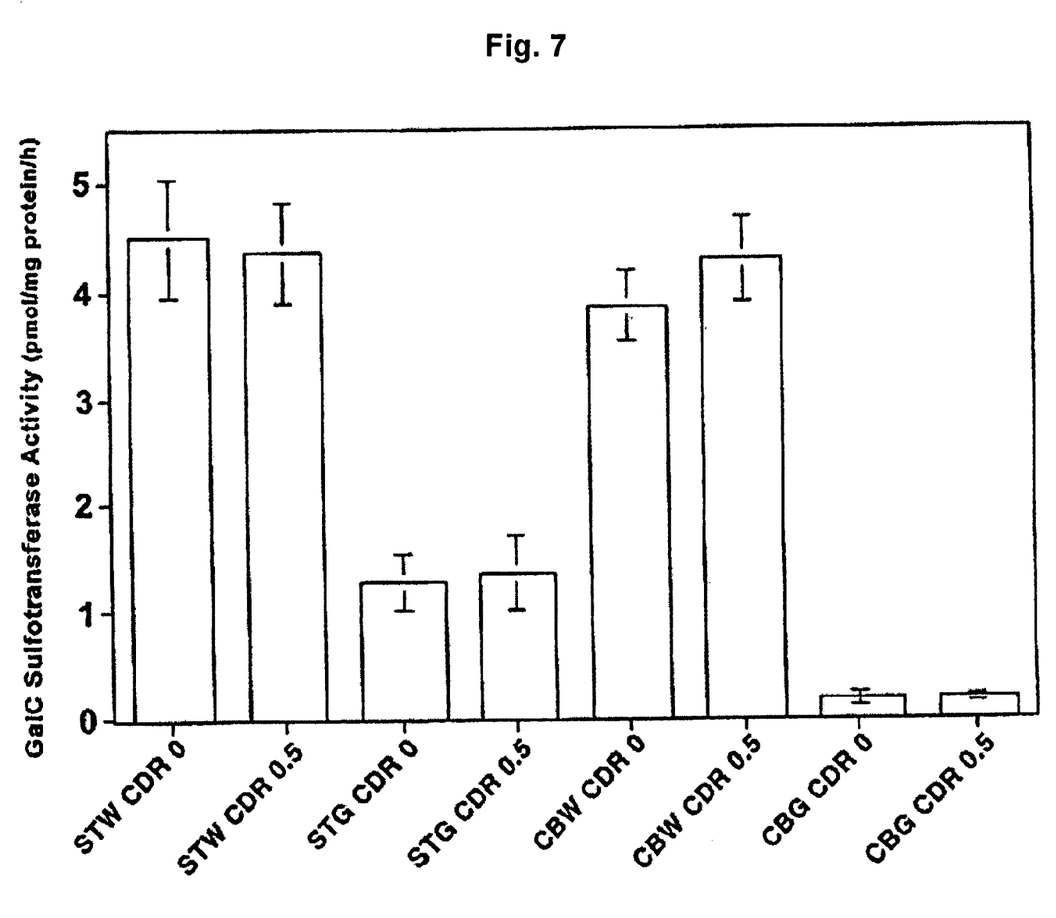
FIG. 7 shows comparisons of galactocerebroside sulfotransferase activity in microsomal preparations of white and gray matter from normal and mild Alzheimer's disease subjects.

The level of galactocerebroside sulfotransferase activity was also measured as a function of CDR in samples obtained from the brain bank of Washington University ADRC Neuropathology/Tissue Research Core from three CDR 0 and three CDR 5 individuals. Enzymatic activity was assayed by quantitation of the reaction product $^{35}$S-labeled sulfatide, and normalized to the protein content. In FIG. 7, STG represents superior temporal gray matter; STW is superior temporal white matter, CBG represents cerebellar gray matter and CBW represents cerebellar white matter. Although there were large differences depending on the source of the sample, no differences were observed between CDR 0 and CDR 5 subjects.

EXAMPLE 2

Determination of Sulfatides in Cerebrospinal Fluid

Figure 8A:
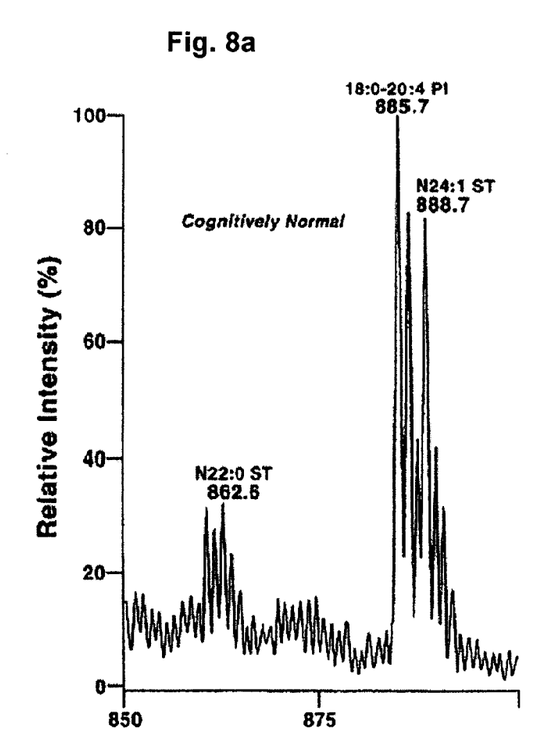
FIGS. 8A and 8B show a comparison of negative ion ESI-mass spectrum of a lipid extract of cerebrospinal fluid from a normal and a mild Alzheimer s disease subject.
Figure 8B:
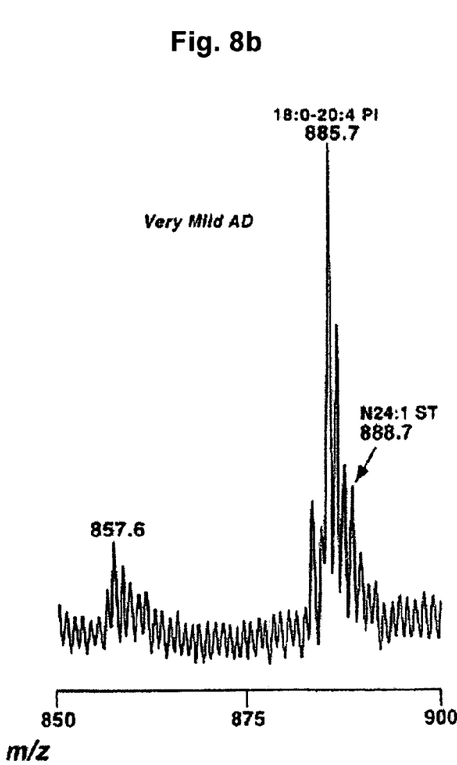

Spinal taps (after overnight fast) were performed on longitudinally followed subjects at the Washington University Memory and Aging Project. Nineteen subjects with a CDR of 0 and 20 subjects with a CDR score of 0.5 were used in the study. None of the subjects had prior history of stroke or other neurological disease. The mean age was 71 for CDR 0 and 72 for CDR 0.5. Sulfatide (ST) and phosphatidyl inositol (PI) levels were measured by ESI-MS, and the ratio of sulfatides to phosphatidyl inositol (ST/PI) was determined. The results are shown for individual samples in FIGS. 8A (CDR 0) and 8B (CDR 0.5). As shown, the level of sulfatides is greatly decreased in the individual with a CDR 0.5 score, while the level of PI is essentially the same for both the CDR 0 and CDR 5 subjects.

The reliability of the CSF ST/PI ratio in 19 CDR 0 and 20 CDR 0.5 subjects was verified in our study using ESI-MS for measurement of the ST/PI ratio. These results are shown in FIGS. 9A–E. Subjects who are cognitively normal (CDR 0) and those with very mild dementia (CDR 0.5) were compared. The lack of severity of the dementia itself is illustrated in FIG. 9E which compares the Mini-Mental State Exam scores (MMSE scores) between the two groups. The mean score is lower in the CDR 0.5 group, but there is a great deal of overlap between individual subjects: CDR 0=29.42±0.18; CDR 0.5=26.35±0.72; p=0.002.

Figure 9A:
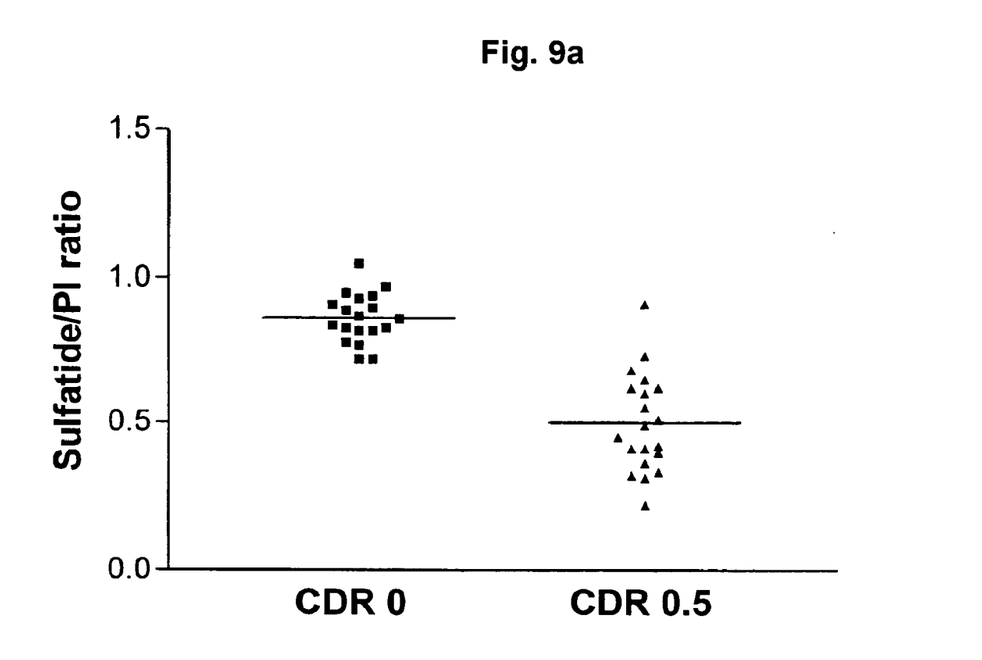
FIG. 9A shows a comparison of the sulfatide/phosphatidylinositol ratio in the cerebrospinal fluid of normal individuals as compared to individuals with very mild dementia.

FIG. 9A shows a dramatic difference between the two groups in terms of the sulfatide/phosphatidylinositol ratio with very little overlap. There were 20 subjects in the CDR 0.5 group and 19 in the CDR 0 group. Only 2 subjects in the CDR 0.5 group overlap with the CDR 0 group: ST/PI ratio (mean±SEM): CDR 0=0.86±0.019; CDR 0.5=0.499±0.38; p<0.0001.

Figure 9B:
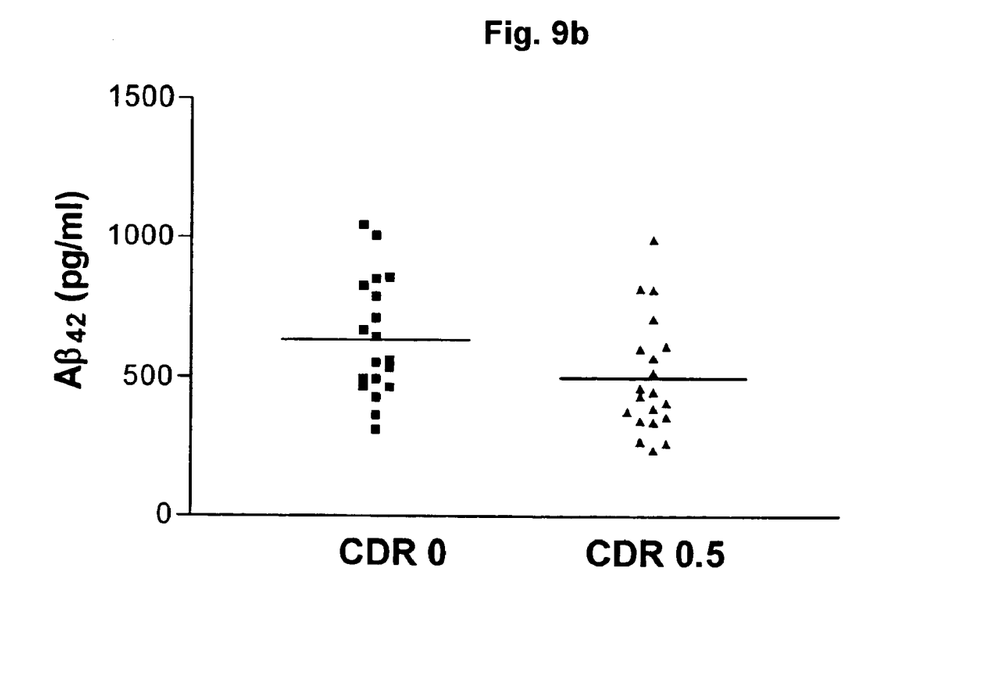
FIGS. 9B–9D show similar comparisons when the levels of $A\beta_{42}$, tau protein, and $pTau_{231}$ were measured.

The superior ability of this method to differentiate the two groups is further illustrated by comparing the results in FIG. 9A with those in FIG. 9B. FIG. 9B shows the results of comparison of levels of $A\beta_{42}$ according to one measure practiced in the prior art. CSF $A\beta_{42}$ is significantly lower in CDR 0.5 than CDR 0 subjects but there is marked overlap between the groups. $A\beta_2$ (mean±SEM, pg/ml): CDR 0=636.6±48.4; CDR 0.5=498.9±45.8; p=0.04.

Figure 9C:
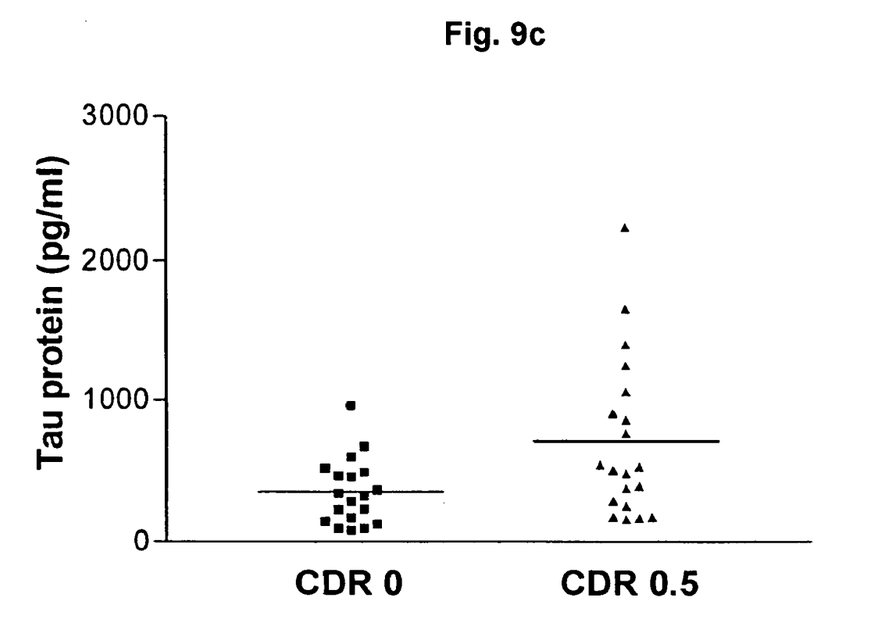
Figure 9D:
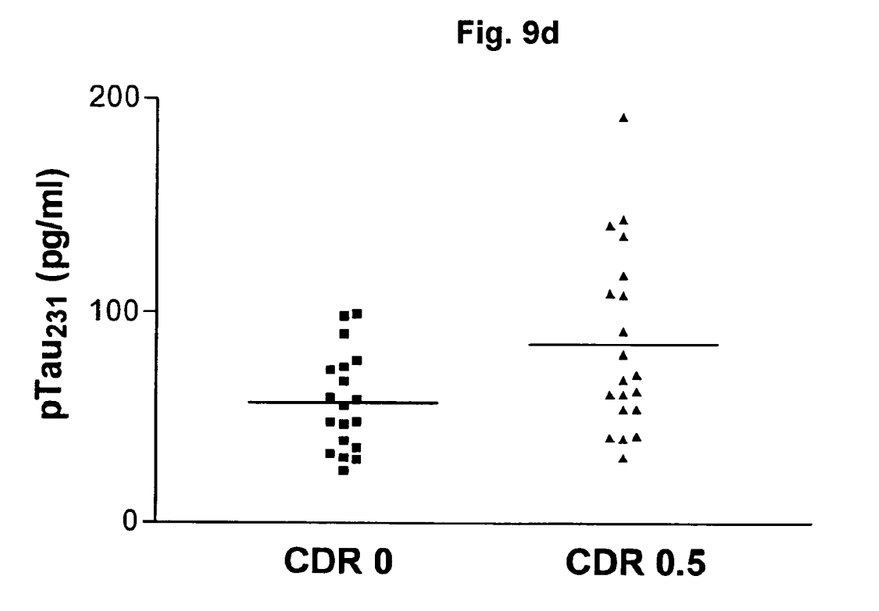
Figure 9E:
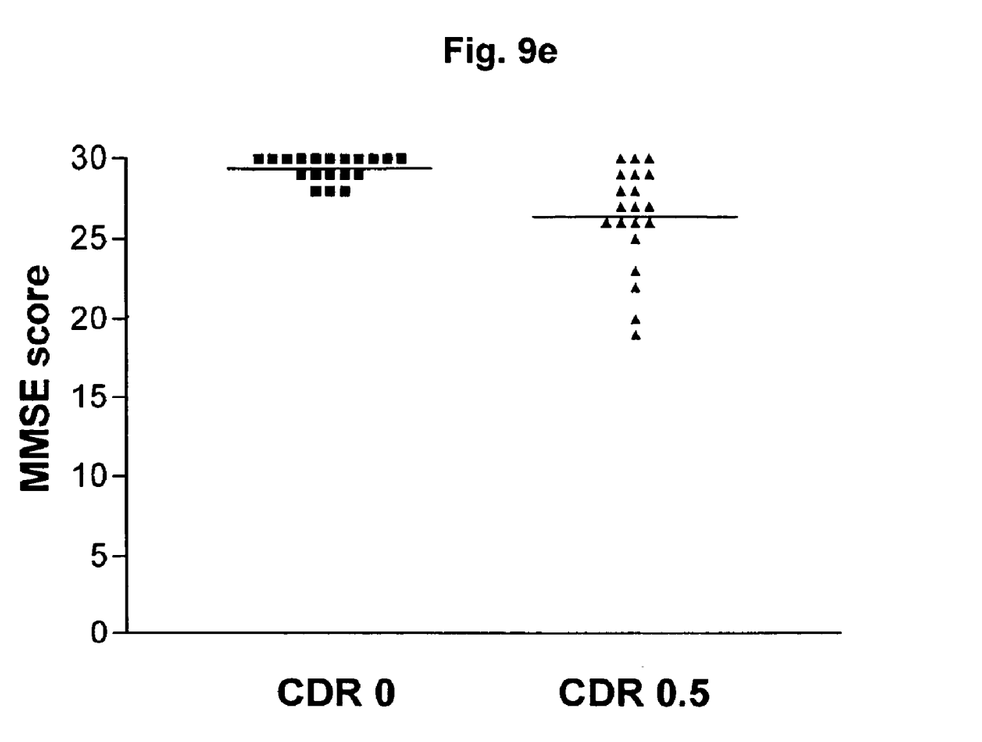
FIG. 9E compares the results of the two groups using a test for cognitive ability.

Similarly, FIGS. 9C and 9D show that other commonly used biomarkers of Alzheimer's disease, while providing different mean values, show significant overlaps. As shown in FIG. 9C, CSF tau is significantly increased in CDR 0.5 subjects (p<0.05) but there is a also a large amount of overlap between CDR 0 and 0.5 subjects. Total tau (mean±SEM, pg/ml): CDR 0=350.5±53.1; CDR 0.5=706.6±126.7; p=0.0153.

Further, as shown in FIG. 9D, CSF $pTau_{231}$ is significantly increased in CDR 0.5 subjects but as for total tau, there is a large amount of overlap between CDR 0 and 0.5 subjects. $pTau_{231}$ (mean±SEM, pg/ml): CDR 0=57.98±15.32; CDR 0.5=85.69±9.61; p=0.0175.

Thus, the invention method provides not only a statistical difference between individuals who are normal and those who have mild dementia but also provides an assay which is applicable to individuals in view of the fact that there is very little overlap between the cognitively normal and very mildly demented groups.

The invention claimed is:

1. A method to identify a subject who is at high risk for, or who has developed, Alzheimer's disease, which method comprises
    (a) assessing the level of sulfatides in a biological fluid of said subject;
    (b) providing the level of sulfatides in the corresponding biological fluid in normal subjects;
    (c) comparing the level of sulfatides assessed in (a) with that of normal subjects as provided in (b);
    wherein when the comparison in (c) shows the level of sulfatides in said subject in (a) is statistically significantly decreased from those in normal subjects as provided in (b),
    said subject is identified as at high risk for, or as a subject who has developed, Alzheimer's disease.

2. The method of claim 1, wherein the biological fluid is plasma, urine, or cerebrospinal fluid.

3. The method of claim 2, wherein the biological fluid is cerebrospinal fluid.

4. The method of claim 1, wherein the level of sulfatides is measured as total sulfatides.

5. The method of claim 1, within the level of sulfatides is measured as the level of a single species of sulfatide.

6. The method of claim 1, wherein the level of sulfatides is normalized to the level of one or more non-variant lipids.

7. The method of claim 6, which the comparing in (c) is of the ratio of sulfatides to one or more non-variant lipids.

8. The method of claim 6, wherein the non-variant lipid is phosphatidyl inositol.

9. The method of claim 1, wherein the biological fluid is cerebrospinal fluid and wherein the sulfatide level is measured as the ratio of total sulfatides to phosphatidylinositol (ST/PI).

10. The method of claim 1, wherein said level of sulfatides is measured using electrospray ionization mass spectrometry.

11. The method of claim 9, wherein said level of sulfatides and of phosphatidyl inositol is measured using electrospray ionization mass spectrometry.

12. A method to identify a subject who is at high risk for, or who has developed Alzheimer's disease, which method comprises
   (a) assessing the level of ceramide in a biological fluid of said subject;
   (b) providing the level of ceramide in the corresponding fluid in normal subjects;
   (c) comparing the level of ceramide assessed in (a) with that of normal subjects as provided in (b);
   wherein when the comparison in (c) shows the level of at least one sulfatide metabolite in said subject in (a) is statistically significantly increased from those of normal subjects provided in (b),
   said subject is identified as at high risk for, or as a subject who has developed, Alzheimer's disease.

13. The method of claim 12, wherein the biological fluid is plasma, urine, or cerebrospinal fluid.

14. The method of claim 13, wherein the biological fluid is cerebrospinal fluid.

15. The method of claim 12, wherein the level of sulfatide metabolites is measured using electrospray ionization mass spectrometry.

* * * * *